(12) United States Patent
Hudkins

(10) Patent No.: US 7,049,483 B1
(45) Date of Patent: May 23, 2006

(54) TRANSGENIC BIOLUMINESCENT PLANTS

(76) Inventor: Bruce Eric Hudkins, 1723 S. Madison Ave., Tulsa, OK (US) 74120

( * ) Notice: Subject to any disclaimer, the term of this patent is extended or adjusted under 35 U.S.C. 154(b) by 532 days.

(21) Appl. No.: 10/195,283

(22) Filed: Jul. 15, 2002

(51) Int. Cl.
*C12N 15/82* (2006.01)
*C12N 15/12* (2006.01)
*C12N 15/53* (2006.01)
*A01H 5/00* (2006.01)

(52) U.S. Cl. ............ 800/282; 800/271; 800/287; 800/288; 800/303; 435/69.8; 435/189

(58) Field of Classification Search ........ 800/271, 800/287, 282, 288, 303; 435/69.8, 189
See application file for complete search history.

(56) References Cited

U.S. PATENT DOCUMENTS

| | | | |
|---|---|---|---|
| 5,093,240 A | 3/1992 | Inoye et al. ............ 435/69.1 |
| 5,162,227 A | 11/1992 | Cormier ............ 435/252.33 |
| 5,221,623 A | 6/1993 | Legocki et al. .......... 435/252.3 |
| 5,422,266 A | 6/1995 | Cormier et al. .......... 435/252.3 |
| 5,583,024 A | 12/1996 | McElroy ............ 135/189 |
| 5,723,765 A * | 3/1998 | Oliver et al. ............ 800/268 |
| 5,728,925 A * | 3/1998 | Herrera-Estrella et al. .. 800/300 |
| 5,741,668 A | 4/1998 | Ward et al. ............ 435/69.1 |
| 5,876,995 A | 3/1999 | Bryan ............ 435/189 |
| 5,976,796 A | 11/1999 | Szalay et al. ............ 435/6 |
| 6,247,995 B1 | 6/2001 | Bryan ............ 446/473 |

OTHER PUBLICATIONS

Matsuo et al. Plant Biotechnology 18(1): 71-75 (Mar. 2001).*
Nass et al. Planta 212(2): 149-154 (2001).*
Plieth et al. pp. 252-253 In: Plant nutrition-Food security and sustainability of agro-ecosystems, Horst et al, eds., Kluwer Academic Publishers: The Netherlands (2001).*
Mayerhofer et al. The Plant Journal 7(6): 1031-1038 (1995).*
Kumar et al. FEBS Letters 268(1): 287-290 (Jul. 1990).*
Knight et al. Journal of Cell Biology 121(1): 83-90 (Apr. 1993).*
Illarionov et al. pp. 223-249 In: Methods in Enzymology, vol. 305, Academic Press (2000).*
Millar et al. The Plant Cell 4: 1075-1087 (Sep. 1992).*
Baruah-Wolff et al. Plant Cell Reports 18(9): 715-720 (1999).*

* cited by examiner

*Primary Examiner*—David T. Fox
(74) *Attorney, Agent, or Firm*—Head, Johnson & Kachigian

(57) ABSTRACT

Transgenic plants are created having incorporated into them a luciferase enzyme gene and a corresponding luciferin substrate gene. These genes are regulated such that for a certain amount of time after dark, these genes are expressed resulting in bioluminescence. Different luciferin/luciferase combinations may be utilized for these transgenic plants, depending on the desired wavelength and the plant species transfected.

18 Claims, 1 Drawing Sheet

TRANSGENIC BIOLUMINESCENT PLANTS

CROSS-REFERENCE TO RELATED APPLICATIONS

Not applicable.

STATEMENT REGARDING FEDERALLY SPONSORED RESEARCH OR DEVELOPMENT

Not Applicable.

REFERENCE TO A SEQUENCE LISTING, A TABLE, OR A COMPUTER PROGRAM LISTING COMPACT DISC APPENDIX

Not Applicable.

BACKGROUND OF THE INVENTION

1. Field of the Invention

The present invention relates to transgenic bioluminescent plants. More specifically, the present invention relates to plants that have been transfected via agro-bacterian or other means known to those in the art with genes encoding luciferase and luciferin such that they may glow in the dark. The transfected genes may be regulated by promoter regions designed to regulate the timing and duration of the genetically engineered bioluminescence.

2. Prior Art

It has been known in the art for some time that certain enzymes called luciferases will bioluminescence in the presence of their substrates, known as luciferins. Luciferases are a broad class of proteins that may be found in bacteria, jelly fish, fireflies and a variety of other organisms. Most luciferases share very little homology with one another and are thought to have evolved relatively independently of each other. Several luciferase genes have been identified and their bioluminescent activities have been used extensively to study gene regulation and expression. By inserting a luciferase protein downstream from a promoter to be studied, one may easily tell when that promoter has been activated by the resulting bioluminescence.

Luciferins tend to be complex organic molecules. Some are thought to be formed by means of complex catabolic pathways. Others, such as coelenterazine, result from the cyclization of amino acids in an expressed polypeptide. Until recently, it has not been possible to isolate a gene capable of forming luciferin in vivo. This has meant that in order to detect luciferase, luciferin must be directly applied to the organism expressing luciferase. Because the luciferin must be absorbed by the cells, individual cells and relatively thin tissue cultures, including very small seedlings, have been the only suitable hosts for studying gene expression using luciferase. Often, the organisms expressing luciferase are lysed and then exposed to a luciferin solution. This obviously kills the host organism.

There has been a significant amount of work done to improve the use of luciferase in studying gene expression. However, they have all been limited by the inability to produce in vivo bioluminescence without the addition of chemicals outside a laboratory environment and in larger organisms.

U.S. Pat. No. 5,093,240 to Inouye et al. discloses the transgenic use of aequorin and derivative polypeptides. This patent discloses the use of a luciferase enzyme in a vector designed for mass production. It is contemplated that the patent will be used to grow large quantities of luciferase in a bacterial culture. It does not disclose the addition of genes capable of forming intracellular luciferin. It also does not contemplate or disclose suitable methods for inserting luciferin into a plant cell.

U.S. Pat. No. 5,162,227 to Cormier also discloses recombinant DNA vectors into which a luciferase enzyme has been inserted. Like the above patent, it contemplates use of these vectors for mass production of luciferase in the bacterial culture. It contemplates use of the luciferase gene as a marker, or selection, gene sequence. It does not contemplate the addition of a luciferin gene into the vector, in vivo bioluminescence or the formation of a transfection vector suitable for plant cells.

U.S. Pat. No. 5,422,266 to Cormier et al. discloses an invention very similar to the one in the above paragraph. It discloses the insertion of a luciferase gene into a vector suitable for use in microorganisms. Like the above mentioned patent, it does not contemplate the additional insertion of a luciferin gene, in vivo biolumiscence or use of vectors suitable for insertion into plant cells.

U.S. Pat. No. 5,583,024 to McElroy et al. discloses use of another luciferase enzyme to be used in a transcription assay. The patent contemplates use of the luciferase to quantify transcription levels of various promoter sequences. It requires lyses, and thus death, of the transformed cells. It does not contemplate in vivo biolumiscence or the addition of a luciferin gene.

U.S. Pat. No. 5,976,796 to Szalay et al. discloses a fusion protein comprising a luciferase and a fluorescing protein. The patent contemplates its use as a double marker in transcription assays. It does not provide for intracellular luciferin or in vivo bioluminescence.

U.S. Pat. No. 5,221,623 to Legocki et al. discloses the use of the lux bacterial luciferase gene in transcription assays of various promoters. It does not contemplate in vivo biolumisence in mature plants or the incorporation of a luciferin gene. Furthermore, the lux bioluminescence mechanism requires a substantial concentration of organic aldehydes. The patent discloses applying aldehyde vapors to the microorganisms. This would be impractical for use in the present invention.

U.S. Pat. Nos. 5,876,995 and 6,247,995 B1 both to Bryan disclose the use of bioluminescent luciferase/luciferin mechanisms for use in a wide variety of novelty items. The luciferase enzyme is added to a large variety of products and the luciferin is added subsequently. This patent does not disclose recombinant uses for luciferase recombinant DNA. However, the specification of this patent is very useful in that it gives a very detailed, textbook-like description of the entire field of bioluminescence.

U.S. Pat. No. 5,741,668 to Ward et al. discloses a polypeptide capable of spontaneously forming coelenterazine in vivo. This is the only patent found in the prior art that contemplates in vivo expression and production of a luciferin. As coelenterazine is difficult to harvest in red pansies and other organisms, this patent contemplates mass producing coelenterazine by expressing and harvesting it in bacterial cultures. It does not contemplate combining this gene with a luciferase gene in a single vector and using that vector to form bioluminescent mature plants.

It is therefore desirable to provide a method for causing bioluminescence in a mature multi cellular organism.

It is also desirable to provide a method for inducing bioluminescence without the need of applying chemicals to an organism.

It is also desirable to provide for a mature plant capable of bioluminescence outside of a laboratory setting and without the need of applying special chemicals.

It is also desirable to provide a mature plant capable of bioluminescence where the timing of that bioluminescence is controlled.

BRIEF SUMMARY OF THE INVENTION

The present invention relates to the use of bioluminescent mechanisms to create transgenic plants that glow in the dark. Although this may be done with any plant, it is generally not preferable to use the present invention with crops. Bioluminescing takes from a plant's energy that could otherwise be used to grow fruit or vegetables. Also, there is a significant amount of controversy relating to genetically modified foods. The general public would probably be reluctant to consume food that glows in the dark. However, despite these drawbacks, there are foreseeable advantages to luminescent crops. Crops capable of producing light facilitate night-time harvesting. Once harvested, they would eventually cease to glow. Assuming that the general public's aversion to genetically modified foods is overcome, this could aid farmers. They could harvest their crops at anytime, including during the cooler evening hours.

It is preferred that common house and landscaping plants be used for the present invention. The present invention enhances the aesthetic qualities of landscape vegetation. The present invention also reduces light pollution and overall energy use. Because the plants themselves illuminate their surroundings, there is no need for landscape lighting and the number of light posts and outdoor lights may be reduced. The softer light of bioluminescence provides for less light pollution than other outdoor lighting. In addition, replacing standard outdoor lighting with bioluminescent plants will result in decreased power usage. This results in a cleaner environment and lower utility bills.

In order to facilitate bioluminescence in plants, at least two genes must be added to the plants. The first is a luciferase enzyme, and the second is a luciferin, the substrate of luciferase. There are many different types of luciferase found in nature. Different luciferases have different luciferins as their substrates. Luciferins are for the most part not interchangeable with other types of luciferase. For example, a firefly luciferase will not induce bioluminescence when exposed to a jellyfish luciferin.

Luciferases and corresponding luciferin have been found in firefly, jellyfish and sea life that live in the bottom of the ocean. For years, they have been used by scientists to study gene regulation and expression in a variety of organisms. Luciferases serve as excellent marker genes because of the ease with which their expression may be detected. Luciferins tend to be complex organic compounds that are oxidized by luciferases. As luciferins are typically not polypeptides, they are produced by complex metabolic pathways. Many of these luciferin catabolic pathways have yet to be elucidated but are believed to require the interaction of several enzymes.

In current genetic expression assays involving bioluminescence, a luciferase gene is spliced downstream from a promoter region to be studied. This recombinant DNA is then inserted into a vector which is subsequently used to transform plant, animal or bacterial cells, depending on a variety of circumstances known to those skilled in the art. The luciferase gene either will or will not be expressed as determined by the promoter region being studied. The cells are then lysed in a bioluminescence buffer and the proper luciferin is added. Emission spectra are then measured. If the sample luminesces it means that the promoter region has induced expression. Those skilled in the art will appreciate that these are common gene expression assays.

Until recently, methods of in vivo production of luciferins were unknown. This is why cells must be lysed and luciferin is then added to them. Typically, luciferins are either organically synthesized or purified from an organism that produces them. This has made luciferins expensive. It has also meant that bioluminescent activity has not been susceptible to transgenic insertion into other organisms. Recently, however, as disclosed in U.S. Pat. No. 5,741,668 to Ward et al., the metabolic pathway for the formation of a luciferin, coelenterrazine has been elucidated.

Coelenterrazine is the substrate for a small group of luciferases found in jellyfishes. This allows a luciferin to be produced within a living cell. Because of this, any organism susceptible to transformation may now be induced to bioluminesce.

In the present invention, a luciferase and pre-coelenterazine are expressed within plant cells. They are preferably only expressed within the leaves of plants. To accomplish this, genes coding for luciferase and pre-coelenterazine are inserted into plant cells by means of a vector. One method of restricting expression of the genes to leaf cells is to include upstream promoter regions specific for leaf cell expression only. Somatic or other plant cells that have been successfully transfected are grown to mature plants. The process of producing mature plants from individual plant cells is well known in the art. A control sequence, such as a rubisco small unit promoter region or the Cab2 promoter (another known circadian clock promoter) sequence is inserted upstream of the luciferase and pre-coelenterazine coding regions. This insures that these two genes are only expressed in the leaves of the plants. Rubisco and Cab2 are down regulated during the nighttime. This means that the two inserted genes will also be down regulated in the dark. This prevents the expression of the inserted genes from placing too much stress on the plant. Because coelenterazine is a fragile organic molecule having a half life of one and a half to two hours, the bioluminescent activity of the plant will cease within three to four hours after dusk. In some cases it may be desirable to utilize a different promoter for the encoded genes. Specifically, it may be desirable to use a promoter that induces expression only in the dark. This would result in the bioluminescence beginning at night and ending at dawn. Those skilled in the art will appreciate that there a large variety of promoters that cause genes downstream from them to be expressed or shut off under a large variety of conditions. Which promoter will be most desirable will depend on the plant variety as well as asethetic factors.

Coelenterazine requires $O_2$ and calcium ions in addition to luciferase in order to induce bioluminescence. It may therefore be desirable to have the luciferase and the coelenterazine peptides targeted to specific organelles. Those skilled in the art will appreciate that there are a variety of known target sequences that may be added to the N'terminus of a polypeptide. This is done by inserting a polynucleotide sequence coding for a targeting sequence at the 5' end of the gene. When the gene is expressed, the target sequence will be included in the polypeptide translated. The target sequence will then direct the polypeptides to a specific organelle. This may be desirable in order to insure that plenty of required co-factors are present. In addition, all polypeptides have an optimum pH. Certain organelles may have an internal pH more preferable for the luciferase and luciferin. Various organelles may also have conditions that improve the stability of various polypeptides. Those skilled in the art will realize that these are only some of many factors that will make targeting the luciferase and luciferin to specific organelles.

Those skilled in the art will also appreciate that it may be desirable to add one or more genes or control sequences to the vector used for transfection. Some promoters used to regulate the inserted bioluminescent genes may require other proteins in order to be activated or deactivated. It is often desirable with transfection vectors to include a selection sequence. The selection sequences code for genes that confer resistance to various antibiotics such as kanamycin and streptomycin. Such selection sequences are generally used to isolate cells that have been successfully transfected. However, bioluminescents has itself been used as an indicator. Therefore, it is not necessary to use a selection sequence. Cells that have been successfully transfected may be induced to bioluminsce and may therefore picked out of cells that have not been transfected.

DETAILED DESCRIPTION OF THE INVENTION

Figure 1:
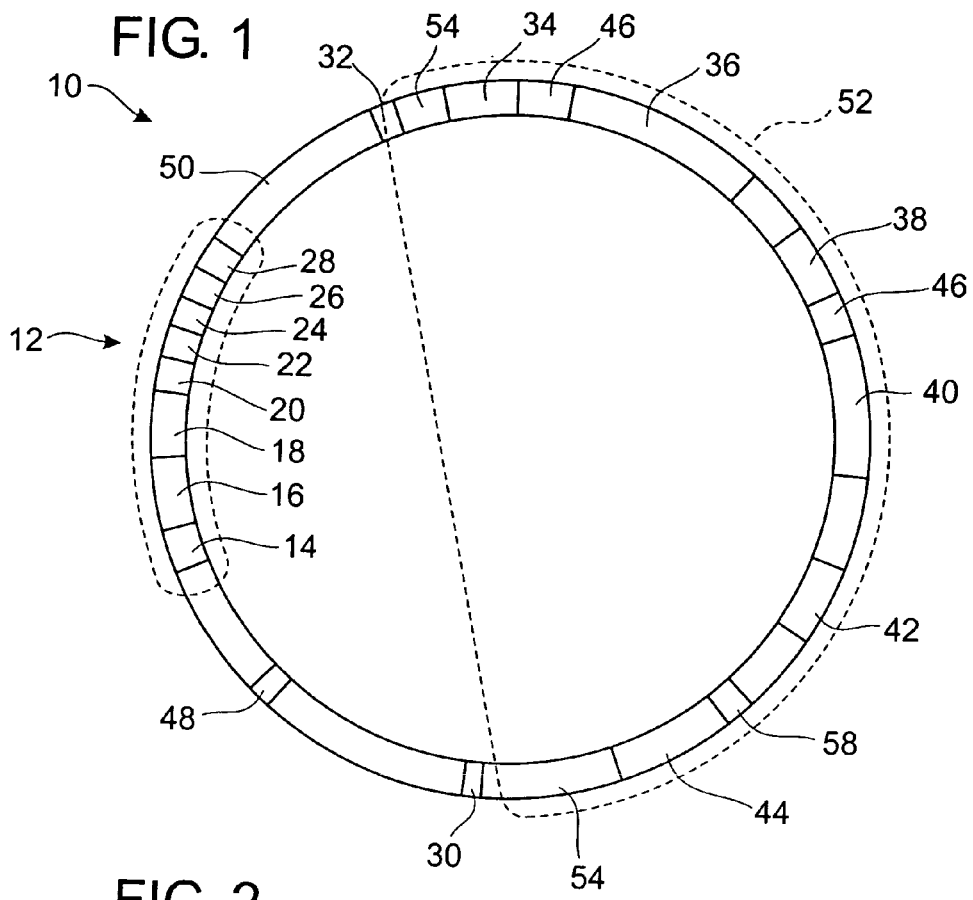
FIG. 1 is a diagrammatic view of a recombinant DNA vector for the present invention.

In describing the present invention, the following terminology will be used in accordance with the definitions set out below. This terminology is well known to those skilled in the art.

"Recombinant polynucleotide" refers to a polynucleotide of genomic, cDNA, semisynthetic, or synthetic origin which, by virtue of its origin or manipulation: (1) is not associated with all or a portion of the polynucleotide with which it is associated in nature, and/or (2) is linked to a polynucleotide other than that to which it is linked in nature, or (3) does not occur in nature.

"Polynucleotide" refers to a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modified, for example by methylation, phosphorylation, and/or by capping, and unmodified forms of the polynucleotide.

"Replicon" refers to any genetic element, e.g., a plasmid, a chromosome, a virus, that behaves as an autonomous unit of polynucleotide replication within a cell; i.e., capable of replication under its own control.

"Vector" is a replicon in which another polynucleotide segment is attached, so as to bring about the replication and/or expression of the attached segment. Vectors may have one or more polynucleotide or recombinant polynucleotide and one or more control sequences.

"Control sequence" refers to polynucleotide sequences which are necessary to effect the expression and/or secretion of coding sequences to which they are ligated. The nature of such control sequences differs depending upon the host organism; in prokaryotes, such control sequences generally include promoter, ribosomal binding site, and terminators; in eukaryotes, generally such control sequences include promoters, terminators and, in some instances enhancers. In addition, in both prokaryotes and eukaryotes, some control sequences direct the expressed polypeptide to a particular location within the cell or region within a multicellular organism. The term "control sequences" is intended to include, at a minimum, all components whose presence is necessary for expression, and may also include additional polynucleotide sequences that influence the expression of a protein.

"Promoter" refers to a polynucleotide sequence upstream from an expressed polynucleotide. A promoter sequence signals the cellular machinery to express the polynucleotide downstream from it. Some promoters operate like a switch and only signal a cell to express a downstream polynucleotide under certain conditions, such as when the organism is under insect/pathogen attack, above a certain temperature, or in the presence of a particular chemical such as IPTG.

"Gene" is a polynucleotide sequence which is transcribed into mRNA and/or translated into a polypeptide when placed under the control of appropriate regulatory sequences. The boundaries of the gene are determined by a translation start codon at the 5'-terminus and a translation stop codon at the 3'-terminus. A gene can include, but is not limited to, mRNA, cDNA, and recombinant polynucleotide sequences.

"Host cells", "microbial cells", "cells" and other terms denoting microorganisms or higher eukaryotic cell lines cultured as unicellular entities, are used interchangeably, and refer to cells which can be, or have been, used as recipients for recombinant vector or other transfer polynucleotides, and include the progeny of the original cell which has been transfected. It is understood that the progeny of a single parental cell may not necessarily be completely identical in morphology or in genomic or total DNA complement as the original parent, due to accidental or deliberate mutation. Progeny of the parental cell which are sufficiently similar to the parent can be characterized by the relevant property, such as the presence of a nucleotide sequence encoding a desired peptide, are included in the progeny intended by this definition, and are covered by the above terms.

"Transformation" or "transfection" refer to the insertion of an exogenous polynucleotide into a microbial cell, or cells of a multicellular organism such as a plant, irrespective of the method used for insertion, for example, direct uptake, transduction, f-mating, particle bombardment or bacteria-mediated gene transfer. The exogenous polynucleotide may be maintained as a non-integrated vector, for example, a plasmid, or alternatively, may be integrated into the host genome.

"Polypeptide" refers to the amino acid product of a sequence encoded within a polynucleotide, and does not refer to a specific length of the product, thus, peptides, oligopeptides, and proteins are included within the definition of polypeptide. This term also does not refer to post-expression modifications of the polypeptide, for example, glycosylations, acetylations, phosphorylations, sialylations, and the like.

Promoters, a subclass of control sequences, are required in order for a polynucleotide to be expressed. There are many known promoters. Which promoter is best for a given transgenic organism will depend on the desired level of expression and the type of organism being transformed.

Those skilled in the art will appreciate that in addition to the wide variety of vectors available for the techniques described herein, there are also a wide variety of control sequences that may be added to a polynucleotide sequence for a variety of reasons. It is possible that in some or all plants bioluminescence will be enhanced by directing the luciferase and corresponding luciferin to a specific location within the plant. This may be accomplished using control sequences that result in the addition of amino acids at either the N-terminus or C-terminus of the proteins. These added amino acids utilize mechanisms within a plant to direct the protein to which they are attached to specific regions of the plant cell. For example, some control sequences direct proteins to the chloroplasts. Some control sequences result in the protein attaching to a membrane. The techniques of utilizing theses control sequences to direct a certain protein to a certain location are well known to those skilled in the art.

It is also well known to those skilled in the art that control sequences may also be used to regulate both the translation and transcription of a polynucleotide sequence. These control sequences may be employed to regulate the concentration of the protein within the organism that is expressing it. The addition of these various types of control sequences to any given vector is a relatively simple procedure.

Some control sequences require the addition of a second, regulatory gene. For example, some control sequences inhibit gene translation only when an inhibitor protein is present. In this situation, it is necessary to add the gene that encodes the inhibitor protein to the vector. This inhibitor protein gene may in turn have its own control sequences upstream or downstream from it. It is even possible for an inhibitor protein gene to have a control sequence that requires a second inhibitor protein gene in order to function properly. However, this is generally not desirable because the more complex a system is, the more likely it is to fail. In addition, just as there are control sequences that require inhibitor proteins, there are also control sequences that require activation proteins that increase gene translation. These control sequences require the addition of an activation protein gene.

There are also control sequences that regulate expression of coding sequences at the transcription stage. These sequences inhibit or facilitate ribosomal activity on mRNA. All of these mechanisms are well known to those skilled in the art.

Which control sequences, promoters and plasmids are used for a particular plant will be depend on the method of transformation, the plant into which the vector is introduced and personal discretion.

"Luciferase" refers to any of a wide variety of enzymes that oxidize a corresponding luciferin thereby causing bioluminsence. The present invention is generally drawn to luciferases found in certain jellyfish. The term luciferase also refers to oxidizing enzymes found in fireflies, bacteria, fish, squids and other organisms capable of bioluminsence.

"Luciferin" refers to other compounds, some of which are derived from oligopeptides and are susceptible to oxidation by a luciferase. In the particular embodiment described below, coelenterazine is the preferred luciferin however, those skilled in the art will appreciate that any luciferin that may be successfully produced inside a plant cell will be suitable for the invention. Aside from jellyfish, different luciferins may be found in jellyfish, bacteria, fish, squids and other organisms.

"Green Fluorescent Protein" or "GFP" refers to a protein that absorbs blue light emitted by coelenterate luciferases and emits green light by means of fluorescence. The Forster energy transfer effect is believed to allow for a highly efficient conversion of blue light to green light. GFP generally is noncovalently bound to a luciferase/luciferin complex. The purpose of changing the wavelength of the bioluminescence is unknown. The pre-coelenterazine polypeptide disclosed herein has the same sequence as GFP, but having a single amino acid substituted.

"Selection sequence" refers to any of a number of polynucleotide sequences that may be placed in a vector to allow successfully transfected cells to be distinguished from cells that have not been transfected. An example of such a selection sequence is a polynucleotide sequence coding for a promoter and gene for kanamycin resistance. Those skilled in the art will appreciate that there are a variety of sequences that encode for antibiotic resistance, that are commonly used to select transfected cells. Those skilled in the art will also appreciate that there are other selections sequences other than those that encode for antibiotic resistance.

"Sterility operon" refers to one or more genes added to a transfection vector that cause a plant or other organism to be incapable of reproduction. Those skilled in the art will appreciate that a successful sterility operon has been developed by and is currently being used by Monsanto Corporation in their ROUNDUP ready™ soybeans. Those skilled in the art will also appreciate that this is only one of many methods of inducing sterility within a plant or other organism. Such methods are described in U.S. Pat. Nos. 5,723,765, 6,297,426 and 6,228,643.

The present invention relates to the use of two or more genes to construct a bioluminescence mechanism within plant cells. The resulting plants will luminesce for at least a portion of the day. It is preferable to have them luminesce in the evening or at least a few hours. It is foreseen of these plants will increase safety, decrease use of electricity, improve the aesthetic qualities of landscaping, and decrease light pollution all by providing illumination. It is the unique combination of recently discovered bioluminescent genes and known vectors for use in transforming or transfecting plant cells that makes this invention possible.

The invention may be applied to any type of plant. The invention is especially desirable in landscaping and houseplants. Trees, shrubs, flowers and grass are desirable plants for use in the present invention. These are plants typically found in the landscaping of a home's curtilage, where increased security and pleasant appearance is highly desirable. Both monocotyledons such as grasses and palms, and dicotyledons, such as trees and most flowers, may be used in the present invention. Current plant transformation techniques, discussed below, now provide for means for genetically modifying any type of plant. Expression of additional genes, especially if the genes are strongly expressed, will consume some of the plant's energy resources. This is typically seen as a disadvantage in transgenic crop plants. However, this actually presents an advantage when it slows the growth of landscaping and garden plants because it reduces the amount of trimming and pruning required. Transgenic bioluminescent grasses will require mowing less often. Bioluminescent shrubbery requires less trimming. This slow down in growth of a transgenic bioluminescent plant is further enhanced by the fact that the bioluminescent reaction, regardless of the luciferase/luciferin complex utilized, consumes $O_2$, ATP, or both.

Luciferases have been known in the art of biochemistry for many years. Their polynucleotide and amino acids sequences, chromosomal loci, crystal structures and active sites have been elucidated. Jellyfish luciferases having coelenterazine as a substrate typically have a tyrosine peptide at its active site. The family of jellyfish luciferases having coelenterazine as its substrate include aequorin, obelin and renilla luciferase. These luciferases, known as coelenterate luciferases, are especially suitable for the present invention. They are capable of oxidizing coelenterazine in the presence of oxygen and calcium. This makes them especially suitable because a gene in coding for a pre-coelenterazine peptide has recently been discovered. However, those skilled in the art will appreciate that once a gene or operon encoding peptides that form a metabolic pathway for a luciferin is elucidated, that particular luciferin/luciferase bioluminescent mechanism will be equally suitable for the present invention. Those skilled in the art will appreciate that some of these metabolic pathways may be rather complicated, involving many precursor molecules. Long, complex metabolic luciferin pathways are generally undesirable. They are more difficult to successfully insert into a plant's genome, are less likely to work properly and may involve the formation of precursor molecules that are harmful or toxic or cause undesirable side reactions with native plant molecules. Simple luciferin metabolic pathways such as that of coelenterazine, are preferred because of their simplicity and higher success rate.

Once a suitable luciferase/luciferin bioluminescence mechanism has been chosen, they are then utilized to transform, or "transfect," eukaryotic cells. Those skilled in the art will appreciate that there are a number of methods for transfecting a plant cell. The most common method of transfecting plant cells is to utilize the "TI" plasmid from *Agrobacterium tumefaciens*. The TI plasmid contains a T-DNA segment that it transfers into the chromosome of a plant cell it has infected. The T-DNA of the wild type *Agrobacterium* may be replaced with a polynucleotide up to 25 Kb long. In the present invention, a luciferase gene, a luciferin gene, promoters, and optional selections sequence and optional additional control sequences, including targeting sequences, may be inserted in the place of T-DNA. Transfection by *Agrobacterium* will then result in a plant cell in which these polynucleotide sequences have been incorporated into its genome. By exposing the plant cell to the appropriate amounts of hormones and nutrients, a fully mature plant may be developed from the single cell.

The *tumefaciens* TI plasmid only transfects dicotyledon cells, limiting its use. However, the *Agrobacterium rhizogenes* has been found to successfully transfect monocotyledon cells utilizing a similar TI plasmid. Those skilled in the art will appreciate that different types of plant cells require different types of plasmids and bacteria in order to successfully transfect plant cells.

Other methods for transforming plant cells exist. For example, the art of biolistics has been utilized to transform plant cells. In this method, metal micro particles are coded with the desired recombinant DNA fragment. This recombinant DNA fragment may be the same polynucleotide described above having genes and control sequences. The DNA coded microparticles are then accelerated using gunpowder, helium gas or other methods known to those skilled in the art to a suitable velocity such that it may penetrate the plant cell. One of the advantages to biolistics is that it can be utilized on any plant cell. Transfection using a bacteria as described in the previous paragraph is limited to the types of plants which a certain bacteria will infect. The disadvantages of biolistics are that it is expensive and difficult.

Micro-injection is another alternative method of transforming plants. This involves the use of a microscopic needle to penetrate and inject DNA directly into the plant cell nucleus. This method requires very expensive equipment and is also difficult. However, those skilled in the art will know that micro-injection has been used for many years and for many purposes.

Another transformation method suitable for all plant cell types is electroporation. Electroporation involves shocking the plant cells with a powerful electric pulse. This momentarily disrupts the plant cell membrane causing pores to form in its membrane. Recombinant polynucleotides in the surrounding solution may then enter the plant cell through these pores. While this process is relatively simple, it is more suitable for use with animal and bacterial cells that lack a plant wall. For plant cells, the cell wall must be removed, weakening the plant cell.

Yet another method of transforming plant cells is to expose them to polyethelene glycol (PEG). Exposure of plant cell protoplasts to PEG makes them momentarily permeable. Like electro poration, this allows the DNA in a surrounding solution to simply seep into the cell.

Those skilled in the art will appreciate that there are still other methods of transforming plant cells, including the use of silicone fibers. Which method of transformation is most suitable will depend on a variety of factors known to those skilled in the art. Such factors include, but are not limited to, the type of plant cell being transformed, the type of luciferase and luciferin genes being utilized, the size of the recombinant DNA fragment to be inserted, the available facilities and the relative expenses of the methods.

The TI plasmid of *Agrobacterium tumefaciens* is limited by its maximum 25 kb capacity and that it only transfects dicotyledon cells. These limitations may be overcome by using other vectors. Bacterial artificial chromosomes "BAC's" may be used to transform plant cells with recombinant polynucleotide fragments up to 350 kb long. Furthermore, the TI plasmid from *Agrobacterium rhizogenes* has been found to successfully transfect monocotyledon cells. Binary vectors, like the pBIN 20 vector are plasmids that contain the TI plasma and bordered sequences, allowing them to also transfect plant cells.

In plant cells transformed and grown into a mature plant, the bioluminescent mechanism encoding in the recombinant DNA will be expressed according to the promoter used and cause the plant to bioluminesce. So far, bioluminescence in plants has only been achieved by inserting a luciferase gene into plant cells and then growing the cells in a medium on a petri dish and spraying a luciferin on them. The plant cells then take up the luciferin and bioluminesce. This process would not work on a fully matured plant because the luciferin would be very poorly absorbed by the mature plant cells. Furthermore, spraying an entire grown tree or hedge would be very onerous and time consuming.

In one particular embodiment of the present invention, recombinant TI plasmid 10 is utilized to transfect plant cells. See FIG. 1. Plasmid 10 is comprised of virulence coding region 12, insert region 52 and non-coding regions 50. Non-coding regions 50 do not code for any peptides and have no control sequences. Origin of replication region 48 contains sequences recognized by DNA polymerase and is the point at which replication of the plasmid begins.

Virulence region 12 is a relatively large operon that contains polynucleotides sequences that code for the proteins that cause the *Agrobacterium tumefaciens* to invade plant cells. They consist of virA 14, virB 16, virG 18, virC 20, virD 22, virE 24, virF 26 and virH 28. The proteins and enzymes encoded by these genes detect chemicals released by plants that have been wounded. They then allow attachment to and invasion into a plant cell. They are necessary components of a TI plasmid in order for it to successfully transfect a plant cell. Insertion region 52 contains all of the genes and control sequences to be inserted into a plant's genome. Left border 32 and right border 30 each consist of a 25 bp polynucleotide sequence that is reasonable for inserting an insertion region 52 into the plant genome.

Restriction regions 54 are each comprised of a series of restriction sites. Those skilled in the art will be intimately familiar with restriction sites. They are very short sequences recognized by endonucleases and facilitate splicing of polynucleotide sequences into the T-DNA region. Those skilled in the art will appreciate that the TI plasmid "Agro-Bacterium" *Agrobacterium tumefaciens* has been modified many times by many persons and companies. There are at least several dozen versions of the TI plasmid and the actual restriction sites present on regions 54 will be determined by which modified TI plasmid is used, generally, which restriction sites are used to splice desired insertion region DNA into. The plasmid makes no difference. IT is generally desirable to use different restriction sites on the 5' and 3' ends of an insertion region recombinant DNA. This prevents plasmids from ligating to themselves without an insertion region. However, it is possible to use the same restriction enzyme on both the five prime and three prime ends, it is simply less efficient.

Sequence 36 codes for a luciferase gene. It is regulated by promoter sequence 34. In this particular embodiment, targeting sequence 46 is located at the 5' end of luciferase gene sequence 36. The presence of targeting sequence 46 codes for an additional peptide sequence that is added to the N' terminus end of the luciferase enzyme. This targeting sequence causes the intracellular machinery to direct the luciferase enzyme to a specific organelle or region of the cell. The targeting sequence may direct proteins to a variety of organelles including, but not limited to, the golgi apparatus, mitochondria, chloroplasts, lysosomes, peroxisomes, the nucleosone or other organelles. Including targeting sequence 46 is optional as the luciferase/luciferin reaction will go forward in the cytosol. However, targeting the enzyme and its substrate to a specific organelle may be advantageous for a number of reasons. Various organelles may have optimal pH, higher concentrations of $O_2$, ATP or calcium. Also, directing all of the luciferase and luciferin to an organelle will result in a higher relative concentration of the enzymes and accelerate the reaction. This has the result of shortening the length of time it takes to consume the luciferin, but it also increases the brightness of the bioluminescent plant.

Promoter region 34 may be any of a variety of promoter sequences known in the art. In this particular embodiment, the Cab2 promoter region of the a/b photoactive complex is used. The cab2 promoter down regulates a downstream gene sequence when night falls. This means the luciferase gene will stop being expressed around dusk. Down regulating the foreign gene allows the plant to use its energy and amino acids and ribosomes for other, natural functions. However, it is possible to utilize other promoters that are never turned off. Alternatively, it is possible to utilize promoters that up regulate at night and down regulate during the day. It is known in the art that there are a number of promoter regions relating to the "circadian" clock and regulate genes according to the amount of sunlight they are currently exposed to. Because the bioluminescence of these plants can only be seen in the dark, it is preferred that there bioluminescence be regulated by the amount of light they are exposed to. However, this is not necessary and any desired promoter may be used.

A wide variety of plant promoters are known and may be used to facilitate expression of the bioluminescing machinery in a variety of locations within a plant. In flowering plants, it may be desirable to induce bioluminescence in the flowers themselves. Alternatively, it may be desirable in fruiting plants to induce bioluminescence in the fruit only. The desired location of the bioluminescence, the desired duration and the species of plant will determine the promoter used.

Luciferin coding region 40 is similarly regulated by promoter region 38. It is generally preferable that promoter sequence 34 and promoter sequence 38 are comprised of the same sequence but this is not necessary. In this particular embodiment, the luciferin utilizes coelenterazine and coding region 40 codes for a pre-coelenterazine peptide as the one described in the '668 patent to Ward et al. Once the gene is transcribed and then translated into a polypeptide, the pre-coelenterazine polypeptide spontaneously reacts with itself resulting in a cyclic tripeptide comprised of two tyrosines and a phenylaninine and forming coelenterazine. Because coelenterazine has a relatively short half life of one and a half to two hours, it may be desirable to use a different promoter sequence for promoter 38 than is used for promoter sequence 34. This promoter region 38 is comprised of the Cab2 or other circadian clock promoter that turns off in the nighttime, bioluminescence of this particular embodiment will only last a few hours after dusk. It may be more desirable to utilize a promoter that turns on at dusk. It may also be preferable to utilize a promoter that is not dependent upon the circadian clock.

In this particular embodiment, luciferin gene 40 codes for pre-coelenterazine, a polypeptide. Those skilled in the art will appreciate that other luciferins may require a metabolic pathway and therefore an operon of more than one gene in order to form intracellular luciferin. This embodiment discloses the simplest mechanism. However those skilled in the art will appreciate that the present invention may be comprised of these other more complex operons in place of a single polypeptide. As also known in the art and described herein that the use of an alternative luciferin would require use of an alternative luciferase gene 36.

This particular embodiment also includes a selection sequence 42 coding for kanamycin. Those skilled in the art will appreciate that this is only one of several possible selection sequence. Other ubiquitous antibiotic resistance selections sequences include those that confer resistance to streptomycin and hygromycin. However, those skilled in the art will also appreciate that a selection sequence is not necessary because bioluminescence itself may serve as the selecting marker. However, it is still possible to use antibiotic resistance or other selection markers if desired.

Certain promoter regions require additional genes to assist in regulating them. It is possible to include these genes in insertion region 52. In this particular embodiment, cab2 promoter regions are used and additional control sequences are therefore unnecessary. Those skilled in the art will appreciate that the use of cab2 means that this plasmid will be appropriate for transforming arabidopsis as well as other plants. Which promoter will be used will depend upon the type of plant being transformed as well as the desired timing of the bioluminscence.

Figure 2:
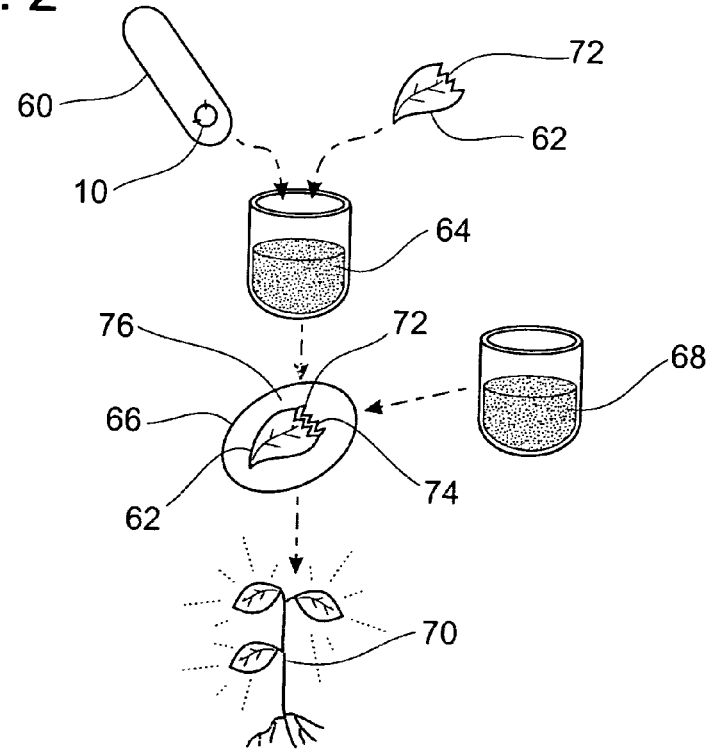
FIG. 2 is a diagrammatic view of a method of forming a transgenic plant of the present invention.

FIG. 2 shows a method for forming a bioluminescent plant utilizing the plasmid shown in FIG. 1. Plasmid 10 is inserted into *Agrobacterium tumefaciens* and is placed in an inoculation solution 64 along with leaf fragment 62. Leaf fragment 62 has torn portions 72 where the leaf has been wounded. Leaf fragment 62 must have a wounded portion in order for *Agrobacterium* to transfect the plant cells within the fragment 62. In fact, the transfected cells of leaf fragment 62 will lie along wounded portion 72. Once leaf fragment 62 has been inoculated, it is transferred to petri dish 66 having growth medium 76. Growth medium 76 has nutrients sufficient to keep transfected cells alive. Leaf fragment 62 now has a region of transfected cells 74 along wounded portion 72. Maturing solution 68 is repeatedly added to petri dish 66. Maturing solutions 68 is comprised of nutrients and hormones that cause the transfected cells to develop into a mature plant. In this particular embodiment, the transfected cells are left on leaf fragment 62 to result in a single transgenic plant 70. However, those skilled in the art will appreciate that each transfected cell may be separated and grown itself into a mature plant. Those skilled in the art will appreciate that this diagram is a simplification of the process and that there are many steps involved and may take several weeks or months to develop a young plant. In the case of transgenic trees and large shrubs, it may be several years before a mature transgenic bioluminescent plant develops.

It may be desirable to insure that these transgenic bioluminescent plants are sterile. People who oppose the genetic modification of organisms may be more accepting of these plants that they are incapable of reproducing. Those skilled in the art will appreciate that methods for making genetically modified organisms sterile have already been developed. Such methods are described in U.S. Pat. Nos. 5,723,765, 6,297,426 and 6,228,643. Those skilled in the art of embryology will appreciate that there are several promoter sequences that are regulated by the age of the organism. When plants first sprout, a number of promoters are turned on and the number of promoters are turned off. Several of these promoters will eventually be turned off as the plant ages and some of the promoters will be turned on as the plant ages. Recombinant polynucleotides having genes to be inserted into a plants genome may include an operon that is activated by an early development promoter sequence. This would cause the operon, illustrated as operon 44 in FIG. 1, to induce production of a toxin which would kill the seedling. This would prevent the plant from producing offspring.

In this particular embodiment, toxin gene sequence 44 codes for a ribosomol inhibitory protein (RIP) that inhibits intracellular machinery. Promoter 58 has any of a number of promoter sequences known to those skilled in the art that are active at the time of germination but shut off shortly afterwards. Sequences 58 and 44 are optional, but would help to decrease the chance of infringement. They would also allay any fears that these plants would overwhelm natural plants.

Whereas, the present invention has been described in relation to the drawings attached hereto, it should be understood that other and further modifications, apart from those shown or suggested herein, may be made within the spirit and scope of this invention.

What is claimed is:

1. A method for making a transgenic bioluminescent plant comprising:
   transfecting at least one plant cell with at least one vector comprising a gene encoding for a luciferase and a gene encoding for a coelenterazine precursor that is compatible with the encoded luciferase;
   growing said at least one plant cell into a mature plant; and,
   providing a means for regulation of expression of said gene encoding for luciferase and said gene encoding for coelenterazine precursor, wherein said means is selected from the group consisting of the rubisco 5' promoter region and the Cab2 promoter region.

2. The method of claim 1 wherein said gene encoding for a luciferase is a gene encoding for aequorin.

3. The method of claim 1 wherein said gene encoding for a luciferase is a gene encoding for obelin.

4. The method of claim 1 wherein said gene encoding for a luciferase is a gene encoding for renilla luciferase.

5. The method of claim 1 wherein said vector further comprises a sterility operon and is incapable of reproduction.

6. The method of claim 5 wherein said sterility operon comprises at least one gene sequence encoding for a toxin having an upstream promoter sequence that is activated at the time of germination but is not activated in a mature plant.

7. The method of claim 6 wherein said toxin is a ribosomal inhibitor protein.

8. The method of claim 1 wherein said means for regulating the expression of said gene encoding for luciferase and said gene encoding for coelenterazine precursor is the rubisco 5' promoter region.

9. The method of claim 1 wherein said gene encoding for a luciferase further includes a targeting sequence such that the expressed polypeptide is directed to a specific organelle.

10. The method of claim 9 wherein said specific organelle is selected from the group consisting of perixosomes, lysosomes, mitochondria, chloroplasts, golgi apparati and nucleoli.

11. The method of claim 1 wherein said plant cell is a monocotyledon cell.

12. The method of claim 1 wherein said plant cell is a dicotyledon cell.

13. A transgenic bioluminescent plant comprising:
   at least one plant cell;
   a recombinant segment of DNA incorporated into the genome of said at least one plant cell;
   wherein said recombinant DNA comprises at least one gene encoding a luciferase and at least one gene encoding for a coelenterazine precursor; and,
   at least one 5' promoter sequence upstream from said gene encoding a luciferase and at least one 5' promoter sequence upstream from said at least one gene encoding for at least one coelenterazine precursor wherein said 5' promoter sequences are selected from the group consisting of the rubisco 5' promoter region and the Cab2 promoter region.

14. The plant of claim 13 wherein said gene encoding for a luciferase encodes for aequorin.

15. The plant of claim 13 wherein said gene encoding for a luciferase encodes for obelin.

16. The plant of claim 13 wherein said gene encoding for a luciferase encodes for renilla luciferase.

17. The plant of claim 13 wherein said recombinant segment of DNA further comprises a sterility operon and is incapable of reproduction.

18. The plant of claim 17 wherein said sterility operon comprises a gene encoding for a toxin having a 5' promoter sequence that is activated at the time of germination but deactivated in mature plants.

* * * * *